US009795792B2

(12) United States Patent
Ellingson

(10) Patent No.: US 9,795,792 B2
(45) Date of Patent: Oct. 24, 2017

(54) EMERGENCY MODE SWITCHING FOR NON-PACING MODES

(75) Inventor: Michael L. Ellingson, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 1420 days.

(21) Appl. No.: 13/035,349

(22) Filed: Feb. 25, 2011

(65) Prior Publication Data

US 2012/0221068 A1 Aug. 30, 2012

(51) Int. Cl.
*A61N 1/36* (2006.01)
*A61N 1/37* (2006.01)
*A61N 1/368* (2006.01)

(52) U.S. Cl.
CPC ......... *A61N 1/3718* (2013.01); *A61N 1/3688* (2013.01)

(58) Field of Classification Search
CPC ........................... A61N 1/3688; A61N 1/3718
USPC .................................................. 607/2, 9, 17
See application file for complete search history.

(56) References Cited

U.S. PATENT DOCUMENTS

| 4,390,020 | A | 6/1983 | Herpers |
|---|---|---|---|
| 5,629,622 | A | 5/1997 | Scampini |
| 5,697,958 | A | 12/1997 | Paul et al. |
| 6,636,766 | B2 | 10/2003 | Bornzin et al. |
| 7,164,950 | B2 | 1/2007 | Kroll et al. |
| 7,369,898 | B1 | 5/2008 | Kroll et al. |
| 7,509,167 | B2 | 3/2009 | Stessman |
| 7,561,915 | B1 | 7/2009 | Cooke et al. |
| 2003/0144705 | A1 | 7/2003 | Funke |
| 2005/0231374 | A1 | 10/2005 | Diem et al. |
| 2006/0167496 | A1 | 7/2006 | Nelson et al. |
| 2006/0271118 | A1* | 11/2006 | Libbus et al. ................ 607/9 |
| 2007/0238975 | A1 | 10/2007 | Zeijlemaker |
| 2009/0138058 | A1 | 5/2009 | Cooke et al. |
| 2009/0157146 | A1 | 6/2009 | Linder et al. |
| 2010/0106227 | A1 | 4/2010 | Min et al. |
| 2010/0121179 | A1 | 5/2010 | Min |
| 2010/0131033 | A1 | 5/2010 | Cantatore et al. |
| 2010/0292745 | A1 | 11/2010 | Shuros et al. |

FOREIGN PATENT DOCUMENTS

EP 58603 8/1982

OTHER PUBLICATIONS (PCT/US2012/0020420) PCT Notification of Transmittal of the International Search Report and the Written Opinion of the International Searching Authority, 11 pages.

* cited by examiner

*Primary Examiner* — Michael D Abreu

(57) ABSTRACT

An implantable medical device (IMD) may be configured into a sensing only mode in which the IMD does not delivery therapy. For example, the IMD may be configured to operate in a sensing only mode to reduce the undesirable effects that may be caused by external fields, such as those generated by an MRI device. However, there may be instances, such as a change in the patient's condition, in which it may be desirable to transition from the sensing only mode to a pacing mode to provide therapy. In accordance with the techniques described herein, the IMD monitors signals on one or more leads coupled to the medical device while operating in the sensing only mode and transitions to a pacing mode in response to not detecting a minimum number of signals on the one or more leads.

20 Claims, 4 Drawing Sheets

EMERGENCY MODE SWITCHING FOR NON-PACING MODES

TECHNICAL FIELD

This disclosure relates generally to implantable medical devices. In particular, this disclosure describes techniques for transitioning operation of an implantable medical device between various operating modes.

BACKGROUND

A wide variety of implantable medical systems that deliver a therapy or monitor a physiologic condition of a patient have been clinically implanted or proposed for clinical implantation in patients. The implantable medical system may include an implantable medical lead connected to an implantable medical device (IMD). For example, implantable leads are commonly connected to implantable pacemakers, defibrillators, cardioverters, or the like, to form an implantable cardiac system that provides electrical stimulation to the heart or sensing of electrical activity of the heart. The electrical stimulation pulses can be delivered to the heart and the sensed electrical signals can be sensed by electrodes disposed on the leads, e.g., typically near distal ends of the leads. Implantable leads are also used in neurological devices, muscular stimulation therapy, gastric system stimulators and other implantable medical devices (IMDs).

Occasionally, patients that have implantable medical systems may benefit, or even require, various medical imaging procedures to obtain images of internal structures of the patient. One common medical imaging procedure is magnetic resonance imaging (MRI). MRI procedures may generate higher resolution and/or better contrast images (particularly of soft tissues) than other medical imaging techniques. MRI procedures also generate these images without delivering ionizing radiation to the body of the patient, and, as a result, MRI procedures may be repeated without exposing the patient to such radiation.

During an MRI procedure, the patient or a particular part of the patient's body is positioned within an MRI device. The MRI device generates a variety of magnetic and electromagnetic fields to obtain the images of the patient, including a static magnetic field, gradient magnetic fields, and radio frequency (RF) fields. The static MRI field may be generated by a primary magnet within the MRI device and may be present prior to initiation of the MRI procedure. The gradient magnetic fields may be generated by electromagnets of the MRI device and may be present during the MRI procedure. The RF magnetic field may be generated by transmitting/receiving coils of the MRI device and may be present during the MRI procedure. If the patient undergoing the MRI procedure has an implantable medical system, the various fields produced by the MRI device may have undesirable effects on the medical leads and/or the IMD to which the leads are coupled. For example, the gradient magnetic fields or the RF fields generated during the MRI procedure may induce energy on the implantable leads (e.g., in the form of a current), which may cause oversensing by the IMD.

SUMMARY

In some situations, an IMD may be configured into a sensing only mode in which the IMD does not delivery therapy. For example, the IMD may be configured to operate in a sensing only mode to reduce the undesirable effects that may be caused by external fields, such as those generated by an MRI device during an MRI procedure. However, there may be instances, such as a change in the patient's condition, in which it may be desirable to transition from the sensing only mode to a pacing mode to provide therapy. In accordance with the techniques described herein, the IMD monitors signals on one or more leads coupled to the medical device while operating in the sensing only mode. In response to not detecting a minimum number of signals on the one or more leads, the IMD transitions to a pacing mode. The reduction of sensed signals below the minimum level may correspond with the need for pacing support to prevent syncope or other adverse events.

In one example, this disclosure is directed to a method comprising configuring an implantable medical device to operate in a first operating mode in which the implantable medical device does not provide pacing and monitor signals on at least one lead while operating in the first operating mode. The method also includes automatically configuring the implantable medical device from the first operating mode to a second operating mode in which the implantable medical device provides pacing upon failing to sense a minimum number of signals on the at least one lead while operating in the first operating mode.

In another example, this disclosure is directed to an implantable medical system comprising at least one implantable medical lead that includes at least one electrode and an implantable medical device connected to the medical lead. The implantable medical device is configured to operate in a first operating mode in which the implantable medical device does not provide pacing, monitor signals on the lead while operating in the first operating mode and transition to a second operating mode in which the implantable medical device provides pacing upon failing to sense a minimum number of signals on the at least one lead while operating in the first operating mode.

In a further example, this disclosure is directed to a computer-readable medium comprising instructions that, when executed, cause an implantable medical device to configure an implantable medical device to operate in a first operating mode in which the implantable medical device does not provide pacing and monitor signals on at least one lead while operating in the first operating mode. The computer-readable medium also includes instructions that, when executed, cause the implantable medical device to automatically configure from the first operating mode to a second operating mode in which the implantable medical device provides pacing upon failing to sense a minimum number of signals on the at least one lead while operating in the first operating mode.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
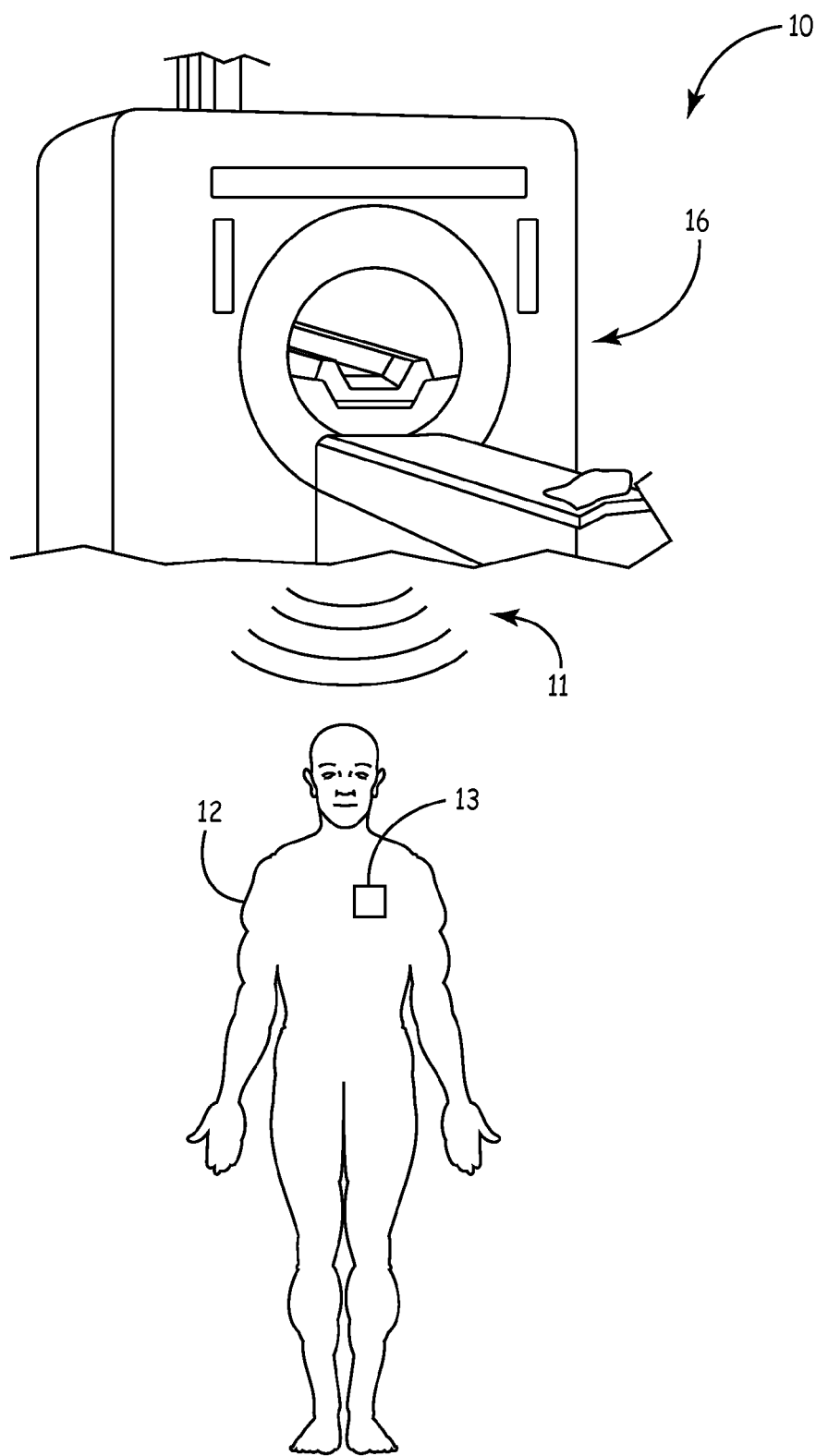
FIG. 1 is a conceptual diagram illustrating an environment in which an implantable medical device is exposed to a disruptive field.

FIG. 1 is a conceptual diagram illustrating an environment 10 in which an implantable medical system 13 is exposed to external fields 11. In the example illustrated in FIG. 1, environment 10 includes an MRI device 16 that generates external fields 11. MRI device 16 generates magnetic and RF fields to produce images of body structures for diagnosing injuries, diseases and/or disorders. In particular, MRI device 16 generates a static magnetic field, gradient magnetic fields and RF fields as is well known in the art. The static magnetic field is a non time-varying magnetic field that is typically always present around MRI device 16 whether or not an MRI procedure is in progress. Gradient magnetic fields are pulsed magnetic fields that are typically only present while the MRI procedure is in progress. RF fields are pulsed high frequency fields that are also typically only present while the MRI procedure is in progress.

The magnitude, frequency or other characteristic of the static magnetic field, gradient magnetic fields and RF fields may vary based on the type of MRI device producing the field or the type of MRI procedure being performed. A 1.5 T MRI device, for example, will produce a static magnetic field of about 1.5 Tesla and have a corresponding RF frequency of about 64 MHz while a 3.0 T MRI device will produce a static magnetic field of about 3.0 Tesla and have a corresponding RF frequency of about 128 MHz. However, other MRI devices may generate different fields.

Implantable medical system 13 may, in one example, include an IMD connected to one or more leads. The IMD may be an implantable cardiac device that senses electrical activity of a heart of patient 12 and/or provides electrical stimulation therapy to the heart of patient 12. For example, the IMD may be an implantable pacemaker, implantable cardioverter defibrillator (ICD), cardiac resynchronization therapy defibrillator (CRT-D), cardioverter device, or combinations thereof. The IMD may alternatively be a non-cardiac implantable device, such as an implantable neurostimulator or other device that provides electrical stimulation therapy.

Figure 2:
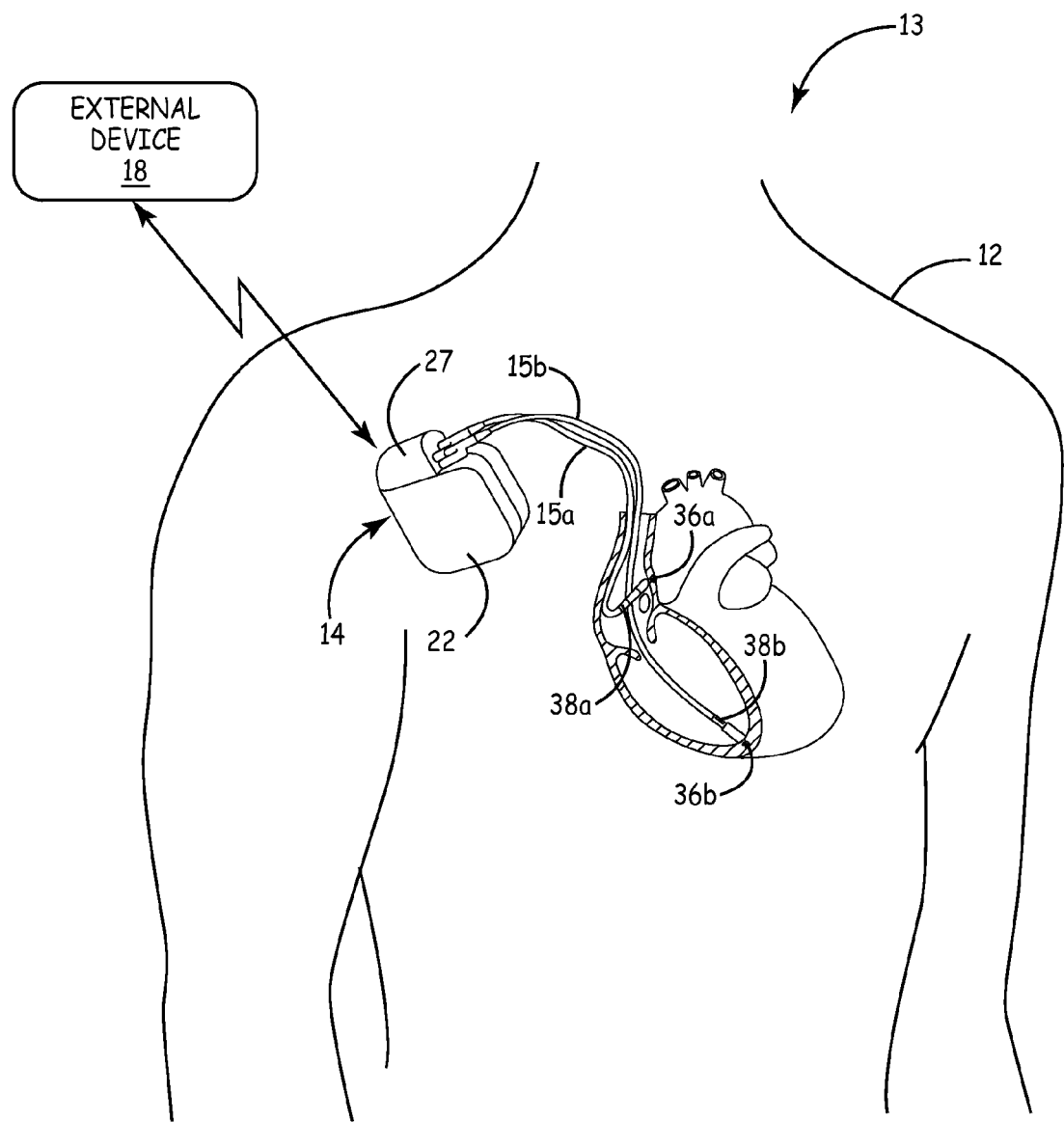
FIG. 2 is a conceptual diagram illustrating an example therapy system that may be used to provide therapy to a patient.

FIG. 2 is a conceptual diagram illustrating an example implantable medical system 13. Implantable medical system 13 includes an IMD 14 connected to leads 15a,b. IMD 14 includes a housing 22 within which electrical components and a power source of IMD 14 are housed. Housing 22 can be formed from conductive materials, non-conductive materials or a combination thereof. As will be described in further detail herein, housing 22 may house one or more processors, memories, transmitters, receivers, sensors, sensing circuitry, therapy circuitry and other appropriate components.

Leads 15a,b each include a respective tip electrode 36a,b and ring electrode 38a,b located near a distal end of their respective leads 15a,b. In other examples, however, leads 15a,b may include more or fewer electrodes. Leads 15a,b may also include a fixation mechanism to affix the tip electrodes 36a,b and/or ring electrodes 38a,b relative to or in a selected tissue, muscle, nerve or other location within the patient 12. The fixation mechanism can be near tip electrodes 36a,b or define a portion of the tip electrodes 36a,b. In the example illustrated in FIG. 2, tip electrodes 36a,b are formed to define the fixation mechanism. Tip electrodes 36a,b take the form of extendable helically shaped electrodes to facilitate fixation of the distal end of leads 15a,b to patient 12. In other instances, the fixation mechanism may be a separate structure from tip electrode 36a,b. Fixation mechanisms can be any appropriate type, including a grapple mechanism, a helical or screw mechanism, a drug-coated connection mechanism in which the drug(s) serves to reduce infection and/or swelling of the tissue, or other attachment mechanism.

Leads 15a,b are connected to IMD 14 via connector block 27. Connector block 27 may include one or more receptacles that interconnect with one or more connector terminals located on the proximal end of leads 15a,b. Leads 15a,b are ultimately electrically connected to one or more of the electrical components within housing 22.

One or more conductors (not shown in FIG. 2) can extend within leads 15a,b from connector block 27 to engage the ring electrode 38a,b and tip electrode 36a,b, respectively. The body of leads 15a,b may be formed from a non-conductive material, including silicone, polyurethane, fluoropolymers, mixtures thereof, and other appropriate materials, shaped to form a lumen within which the one or more conductors extend. In this manner, each of tip electrodes 36a,b and ring electrodes 38a,b is electrically coupled to a respective conductor within its associated lead bodies. For example, a first electrical conductor can extend along the length of body of lead 15a from connector block 27 and electrically couple to tip electrode 36a and a second electrical conductor can extend along the length of the body of lead 15a from connector block 27 and electrically couple to ring electrode 38a. The respective conductors may electrically couple to circuitry, such as a therapy module or a sensing module, of IMD 14 via connections in connector block 27. The electrical conductors transmit therapy from the therapy module within IMD 14 to one or more of electrodes 36a,b and 38a,b and transmit sensed electrical signals from one or more of electrodes 36a,b and 38a,b to the sensing module within IMD 14.

The configuration of implantable medical system 13 illustrated in FIG. 2 is merely an example. In other examples, implantable medical system 13 may include more or fewer leads extending from IMD 14. For example, IMD 14 may be coupled to three leads, e.g., a third lead implanted within a left ventricle of the heart of patient 12. In another example, IMD 14 may be coupled to a single lead that is implanted within either an atrium or ventricle of the heart of patient 12. As such, IMD 14 may be used for single chamber or multi-chamber cardiac rhythm management therapy.

In addition to more or fewer leads, each of the leads may include more or fewer electrodes. In instances in which IMD 14 is used for therapy other than pacing, e.g., defibrillation or cardioversion, the leads may include elongated electrodes, which may, in some instances, take the form of a coil. IMD 14 may deliver defibrillation or cardioversion shocks to the heart via any combination of the elongated electrodes and housing electrode. As another example, medical system 13 may include leads with a plurality of ring electrodes, e.g., as used in some implantable neurostimulators, without a tip electrode or with one of the ring electrodes functioning as the "tip electrode".

IMD 14 may communicate with an external device 18, such as a programmer device. IMD 14 may communicate with external device 18 to provide sensed physiological signals or diagnostic determinations made based on the sensed signals. In the case of a cardiac IMD, IMD 14 may communicate with external device 18 to provide electrical signals from the heart, intracardiac or intravascular pressure, activity, posture, respiration, thoracic impedance, trends of a heart rhythm, or detected cardiac arrhythmia episodes. As another example, IMD 14 may communicate with external device 18 to provide information regarding the performance or integrity of IMD 14 or other components of therapy system 20, such as leads or a power source of IMD 14.

External device 18 may also communicate with IMD 14 to program IMD 14. External device 18 may, for example, communicate with IMD 14 to specify parameters for electrical stimulation therapies, e.g., a therapy progression, select an electrode or combination of electrodes of leads 15a,b to use for delivering electrical stimulation (pulses or shocks), select parameters for the electrical pulse or shock (e.g., pulse amplitude, pulse width, or pulse rate), select electrodes or sensors for use in detecting a physiological parameter of patient 12, or the like.

External device 18 may be a dedicated hardware device with dedicated software for programming of IMD 14. Alternatively, external device 18 may be an off-the-shelf computing device running an application that enables external device 18 to program IMD 14. In some examples, external device 18 may be a handheld computing device or a computer workstation. External device 18 may, in some instances, include a programming head that may be placed proximate to the patient's body near the implant site of IMD 14 in order to improve the quality or security of communication between IMD 14 and external device 18. External device 18 may include a user interface that receives input from the user and/or displays data to the user.

External device 18 may communicate with IMD 14 via wireless communication using any techniques known in the art. Examples of communication techniques may include, for example, inductive telemetry, low frequency telemetry or radiofrequency (RF) telemetry, but other techniques are also contemplated. In some instances, external device 18 and IMD 14 may communicate in the 402-405 MHz frequency band in accordance with the Medical Implant Communications Service (MICS) protocol.

Some or all of the various types of fields produced by MRI device 16 (which are represented by external field 11) may have undesirable effects on implantable medical system 13. In one example, the gradient magnetic fields and/or the RF fields generated during the MRI procedure may induce energy on the conductors of leads 15a,b (e.g., in the form of a current). The induced energy on leads 15a,b may be conducted to IMD 14 and inappropriately detected as physiological signals. The detection of the induced energy on leads 15a,b as physiological signals may result in IMD 14 delivering therapy when it is not desired (e.g., triggering a pacing pulse) or withholding therapy when it is desired (e.g., inhibiting a pacing pulse).

To reduce the undesirable effects the external fields 11 may have on IMD 14, IMD 14 may be configured to operate in an operating mode that is less susceptible to effects that oversensing caused by the induced energy on leads 15a,b may have on pacing. For example, IMD 14 may be configured to operate in a sensing only mode in which IMD 14 continues to sense, but does not provide therapy. IMD 14 may be configured to operate in the sensing only mode when patient 12 is not pacemaker-dependent. For patients that are pacemaker-dependent, IMD 14 may be configured to operate in an asynchronous pacing mode instead of a sensing only mode. In the asynchronous pacing mode, pacing therapy is provided, but not as a function of the sensing.

Even for a patient that is determined to not be pacemaker-dependent at the time of programming to the sensing only mode, it may be desirable to transition from the sensing only mode to a pacing mode should therapy later be desired. In accordance with the techniques described herein, IMD 14 monitors signals on one or both of leads 15a,b during operation in the sensing only mode and transitions to a pacing mode in response to not detecting signals on one or both of leads 15a,b. In one example, IMD 14 may transition from the sensing only mode to a pacing mode in response to not detecting a signal on one or both leads 15a,b for a threshold period of time, e.g., two seconds, three seconds, four seconds or the like.

After the MRI procedure is completed, IMD 14 may transition back to the normal operating mode. IMD 14 may automatically revert to the normal operating mode in response to no longer detecting environment 10, after expiration of a timer or a combination thereof. Alternatively, IMD 14 may be manually programmed into the normal operating mode via a command received from external device 18.

Although described mainly in the context of MRI procedures, the techniques of this disclosure may also allow the patient to undergo other medical procedures that generate external fields (such as high frequency RF signals) that may affect operation of IMD 14, such as electrocautery procedures, diathermy procedures, ablation procedures, electrical therapy procedures, magnetic therapy procedures, or the like. In fact, the techniques of this disclosure may be utilized in any context (medical or non-medical) in which IMD 14 is programmed into a sensing only mode, whether or not IMD 14 is exposed to an external field 11.

Figure 3:
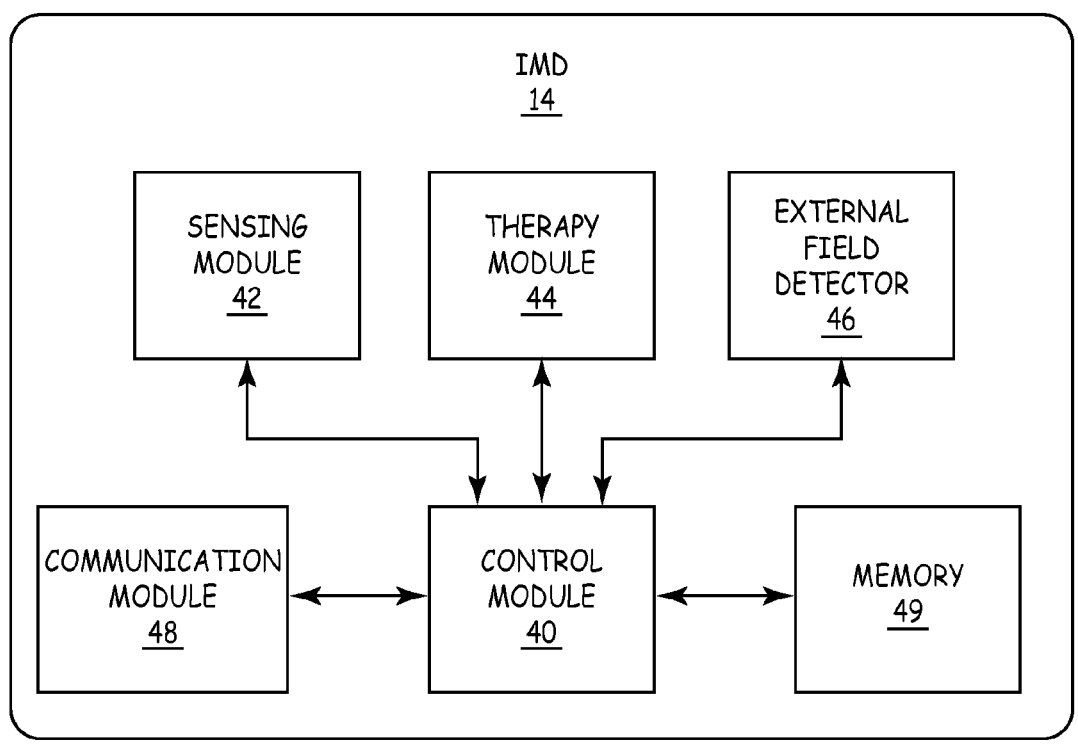
FIG. 3 is a functional block diagram of an example configuration of components of an implantable medical device.

FIG. 3 is a functional block diagram of an example configuration of electronic components of IMD 14. IMD 14 includes a control module 40, sensing module 42, therapy module 44, external field detector 46, communication module 48 and memory 49. The electronic components may receive power from power source (not shown in FIG. 3). In other examples, IMD 14 may include more or fewer electronic components. In addition, any of the described modules or components may be implemented together or separately as discrete but interoperable hardware or software components. Depiction of different features as modules or components is intended to highlight different functional aspects and does not necessarily imply that such modules or units must be realized by separate hardware or software components. Rather, functionality associated with one or more modules may be performed by separate hardware or software components, or integrated within common or separate hardware or software components.

Memory 49 may include computer-readable instructions that, when executed, cause IMD 14 and/or control module 40 to perform various functions attributed to IMD 14 and control module 40 in this disclosure. In other words, memory 49 includes computer-readable instructions that control operation of IMD 14. Memory 49 may, for example, store operating parameters for any of a number of operating modes, including the sensing only mode and any of a variety of pacing modes. Memory 49 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media, or combination thereof.

Control module 40 may include any one or more of a microprocessor, a controller, a digital signal processor (DSP), an application specific integrated circuit (ASIC), a field-programmable gate array (FPGA), or equivalent discrete or integrated circuitry, including analog circuitry, digital circuitry, or logic circuitry. In some examples, control module 40 may include multiple components, such as any combination of one or more microprocessors, one or more controllers, one or more DSPs, one or more ASICs, or one or more FPGAs, as well as other discrete or integrated logic circuitry. The functions attributed to control module 40 herein may be embodied as software, firmware, hardware or any combination thereof.

Control module 40 may communicate with therapy module 44 and sensing module 42. Therapy module 44 and sensing module 42 are electrically coupled to some or all of electrodes 36a,b and 38a,b via the conductors of leads 15a,b. Sensing module 42 is configured to obtain signals from leads 15a,b. Control module 40 may process the signals from leads 15a,b to monitor electrical activity of the heart of patient 12. Control module 40 may, for example, generate electrogram (EGM) waveforms based on the signals received from sensing module 42. Control module 40 may also generate marker channel data based on the detected cardiac activity. For example, marker channel data may include data that indicates the occurrence and timing of sensing, diagnosis, and therapy events associated with IMD 14. Control module 40 may store EGM waveforms and marker channel data in memory 49. Control module 40 may later retrieve stored EGMs from memory 49, e.g., upon a request from external device 18 received via communication module 48. In some examples, control module 40 may detect tachyarrhythmias based on signals received from sensing module 42, e.g., using any suitable tachyarrhythmia detection algorithm. In further examples, sensing module 42 is coupled to one or more sensors that are not included on leads 15a,b, e.g., via a wired or wireless coupling. Such sensors may include pressure sensors, accelerometers, flow sensors, blood chemistry sensors, activity sensors or other types of physiological sensors. Signals monitored by sensing module 42 may be stored in memory 49.

Therapy module 44 is configured to generate and deliver electrical stimulation therapy to the heart. Control module 40 may control therapy module 44 to deliver electrical stimulation therapy to the heart according to one or more therapy programs, which may be stored in memory 49. Control module 40 may, in some instances, control therapy module 44 to deliver therapy to patient 12 as a function of the signals sensed by sensing module 42. For example, control module 40 may control therapy module 44 to trigger and/or inhibit pacing pulses to the heart as a function of the sensed signals received form sensing module 42. In other instances, control module 40 may control therapy module 44 to deliver therapy to patient 12 without regard to signals sensed by sensing module 42, such as in an asynchronous pacing mode.

Therapy module 44 may, under the control of control module 40, also be configured to generate and deliver cardioversion and defibrillation therapy to the heart. For example, in the event that control module 40 detects an atrial or ventricular tachyarrhythmia, control module 40 may load an ATP regimen from memory 49, and control therapy module 44 to implement the ATP regimen. Therapy module 44 may also include a high voltage charge circuit and a high voltage output circuit that generate high voltage shocks to defibrillate the heart.

Communication module 48 includes any suitable hardware, firmware, software or any combination thereof for communicating with another device, such as external device 18 and/or a patient monitor, e.g., by wireless telemetry. For example, communication module 48 may include appropriate modulation, demodulation, frequency conversion, filtering, and amplifier components for transmission and reception of data. Under the control of control module 40, communication module 48 may receive downlink telemetry from and send uplink telemetry to external device 18 with the aid of an antenna (not shown) in IMD 14. Control module 40 may provide the data to be uplinked to external device 18 and the control signals for a telemetry circuitry within communication module 48, e.g., via an address/data bus.

As described above, control module 40 may be configurable to operate IMD 14 in a number of different operating modes. Control module 40 may be configured in some instances to operate IMD 14 in a sensing only mode, such as ODO, OVO or OAO. For example, control module 40 may be configured to operate IMD 14 in the sensing only mode prior to or upon being exposed to environment 10 including MRI device 16 or other device that generates an external field 11. In other instances, control module 40 may be configured into a pacing mode or other therapy mode, such as DDD, VVI, DVI, VDD, AAI, DDI, DDDR, VVIR, DVIR, VDDR, AAIR, DDIR, VOO, AOO or DOO. In the aforementioned pacing modes, the abbreviations of which conform to the NBG Pacemaker Code, the first letter in the pacing mode indicates the chamber or chambers paced and may take on the letter "D" indicating dual chamber (i.e., atrial and ventricle both paced), "V" indicating a ventricle is paced, "A" indicating an atrium is paced, or "O" indicating no chamber is paced. The second letter indicates the chamber or chambers sensed and may take on the letter "D" indicating dual chamber (i.e., atrial and ventricle both sensed), "V" indicating a ventricle is sensed, "A" indicating an atrium is sensed, or "O" indicating no chamber is sensed. The third letter indicates mode or modes of response to sensing and may take on the letter "T" indicating triggered pacing (i.e., pacing is provided in response to the sensing), "I" indicating inhibited pacing (i.e., pacing is stopped based in response to the sensing), "D" indicating dual response (i.e., triggered and inhibited) and "O" for no response. The fourth letter indicates programmable functions and may take on the letter "R" indicating rate modulated pacing, as well as other letters not explained here. Although not described here, a fifth letter may be provided in accordance with the NBG Pacemaker Code indicating anti-tachycardia functions.

External field 11, which may, for example, comprise gradient magnetic fields and/or RF fields produced by MRI scanner 16, may induce energy on one or more of implantable leads 15a,b coupled to IMD 14. In some instances, control module 40 or sensing module 42 inappropriately detects the induced energy on the leads as physiological signals, which may in turn cause undesirable operation of IMD 14. In other words, IMD 14 senses a physiological signal when one is not actually present. When operating in a pacing mode with an inhibit response to sensing, control module 40 may not deliver (i.e., withhold) a desired pacing pulse in response to sensing the induced energy from external field 11 as a physiological signal. When operating in a pacing mode with a trigger response to sensing, control module 40 may deliver an undesirable pacing pulse in response to sensing the induced energy from external field 11 as a physiological signal. In other instances, the induced energy on the leads may result in IMD 14 not sensing actual physiological signals that are present, which may again result in IMD 14 delivering undesired pacing or withholding desired pacing.

To reduce the effects of external field 11, control module 40 may be configured to operate IMD 14 in a sensing only mode prior to or upon being exposed to environment 10 or to external field 11. When operating in the sensing only mode, IMD 14 provides no pacing. Because there is no pacing in the sensing only mode, IMD 14 does not deliver undesirable stimulation or withhold desirable stimulation due to oversensing of noise induced on leads 15*a,b* by external field 11. In the sensing only mode, however, control module 40 and sensing module 42 continue to sense signals on leads 15*a,b*, which may include actual physiological signals of the heart of patient 12 and noise signals induced on leads 15*a,b*. Control module 40 continues to monitor the signals sensed on one or both of leads 15*a,b* to determine whether there is a loss of detected signals.

If such a loss is detected, control module 40 transitions to a pacing mode to provide pacing support. In some instances, control module 40 may control IMD 14 in a manner in which the induced energy on leads 15*a,b* does not affect delivery of therapy. For example, control module 40 may transition to a pacing mode that does not provide sensing functionality, such as an asynchronous pacing mode, e.g., AOO, VOO or DOO. In another example, control module 40 may transition to a pacing mode that includes sensing, but has no mode of response (such as trigger or inhibit) to the pacing, e.g., such as a AAO, AVO, ADO, VVO, VAO, VDO, DDO, DAO or DVO pacing mode. In either of these examples, pacing is provided with no modification due to sensing. As such, the induced energy on the leads caused by external field 11 does not result in undesirable operation of IMD 14. In other instances, control module 40 may transition to a pacing mode responsive to sensing, such as a DDD, VVI, DVI, VDD, AAI, DDI, DDDR, VVIR, DVIR, VDDR, AAIR or DDIR pacing mode. This may be the case when control module 40 does not detect external field 11 at the time that the loss of signals on one or both of leads 15*a,b*.

Control module 40 may be configured to operate IMD 14 in the sensing only mode at some time prior to being exposed. For example, a user, such as a physician, clinician or technician, may manually program control module 40 to operate IMD 14 in the sensing only mode using external device 18. IMD 14 may be manually programmed into the sensing only mode immediately before the MRI procedure, several hours before the MRI procedure, one or more days before the MRI procedure or other time period.

Alternatively, control module 40 may be configured to operate IMD 14 in the exposure mode automatically, e.g., in response to detection of external field 11. IMD 14 may include one or more sensors, such as an external field detector 46, that detect the presence of external field 11. External field detector 46 may include a magnetic field detector, such as a Hall sensor, magnetic gradiometer, or a reed switch. In some instances, external field detector 46 may be within housing 22 of IMD 14. For example, external field detector 46 may be the same field detector used to sense a magnetic programming head of a programming device. Alternatively, IMD 14 may be coupled (wired or wirelessly coupled) to an external field detector 46 located outside of housing 22 of IMD 14. Control module 40 may receive one or more signals from external field detector 46 that identify that IMD 14 has entered an environment in which IMD 14 is exposed to an external field, e.g., a magnetic field, that is greater than or equal to a threshold level indicative of an external field 11.

Even for a patient that is determined to not be pacemaker-dependent at the time of programming to the sensing only mode, it may be desirable to transition from the sensing only mode to a pacing mode should therapy later be desired. As described above, for example, IMD 14 may be programmed into the sensing only mode hours or even days before the MRI procedure. In this case, it may be desirable to transition from the sensing only mode to a pacing mode if the patient's condition changes, e.g., pacing support is required, during the period of time between programming of IMD 14 into the sensing only mode and the MRI procedure. Even in instances in which IMD 14 is programmed into the sensing only mode immediately before the MRI procedure or upon detecting external field 11, it may still be desirable to transition from the sensing only mode to provide pacing support.

As described above, control module 40 continues to monitor the signals sensed on one or both of leads 15*a,b* during the sensing only mode and may transition to a pacing mode in response to not detecting a minimum amount of activity on either one or both of leads 15*a,b* during a period of time. In one example, control module 40 may transition to the pacing mode in response to not detecting a minimum number of signals classified as events for 2-3 seconds on one or both leads 15*a,b*. A signal may be classified as an event when the amplitude of the signal exceeds a threshold. Outside of environment 10, the signals on leads 15*a,b* mainly include sensed cardiac electrical activity. Within environment 10, the signals on leads 15*a,b* may include sensed cardiac electrical activity as well as noise induced on leads 15*a,b* from external field 11. Loss of detection of cardiac events for 2-3 seconds may correspond with the need for pacing support to prevent syncope or other adverse events. As such, IMD 14 may transition from the sensing only mode to the pacing mode before, during or after the MRI or other procedure. In one example, control module 40 may be operating in a sensing only mode that senses signals in the atrium (e.g., OAO) and transition to asynchronous pacing in the atrium (e.g., AOO) if no signals are sensed in the atrium. In another example, control module 40 may be operating in a sensing only mode that senses signals in the ventricle (e.g., OVO) and transition to asynchronous pacing in the ventricle (e.g., VOO) if no signals are sensed in the ventricle. In a further example, control module 40 may be operating in a sensing only mode that senses signals in the atrium and ventricle (e.g., ODO) and transition to a pacing mode that paces both chambers of the heart when no signals are sensed in either of the chambers.

In another example, control module 40 may transition from the sensing only mode to the pacing mode in response to detecting loss of one or more expected cardiac events. Control module 40 may, for instance, transition from the sensing only mode to the pacing mode in response to detecting loss of at least two expected cardiac events within a window of time or within a particular number of expected beats, e.g., missing 2 out of 6 expected events. The expected cardiac events could be determined based on past history of the patient's intrinsic rate. In other instances, control module 40 may detect loss of one or more expected cardiac events by monitoring the intervals between sensed events. For example, control module 40 may transition to the pacing mode when there are two occurrences of sensing intervals that are greater than one second over the past six seconds. In another example, control module 40 may transition to the pacing mode when two of the last six sensing intervals are significantly longer than expected (e.g., at least 25% longer than typical based on past history of intrinsic activity or a predetermined threshold interval). In further instances, control module 40 may detect loss of one or more expected cardiac events by monitoring for ventricular events following sensed atrial events. In this case the ventricular events are the expected events. For example, control module 40 may transition to the pacing mode in response to detecting at least two of the last six atrial events do not have corresponding ventricular events. The examples are provided for illustration purposes only. However, other thresholds, ratios or time intervals may be used.

After the MRI procedure is completed, IMD 14 may transition back to the normal operating mode. IMD 14 may automatically revert to the normal operating mode in response to no longer detecting environment 10, after expiration of a timer or a combination thereof. Alternatively, IMD 14 may be manually programmed into the normal operating mode via a command received from external device 18.

Figure 4:
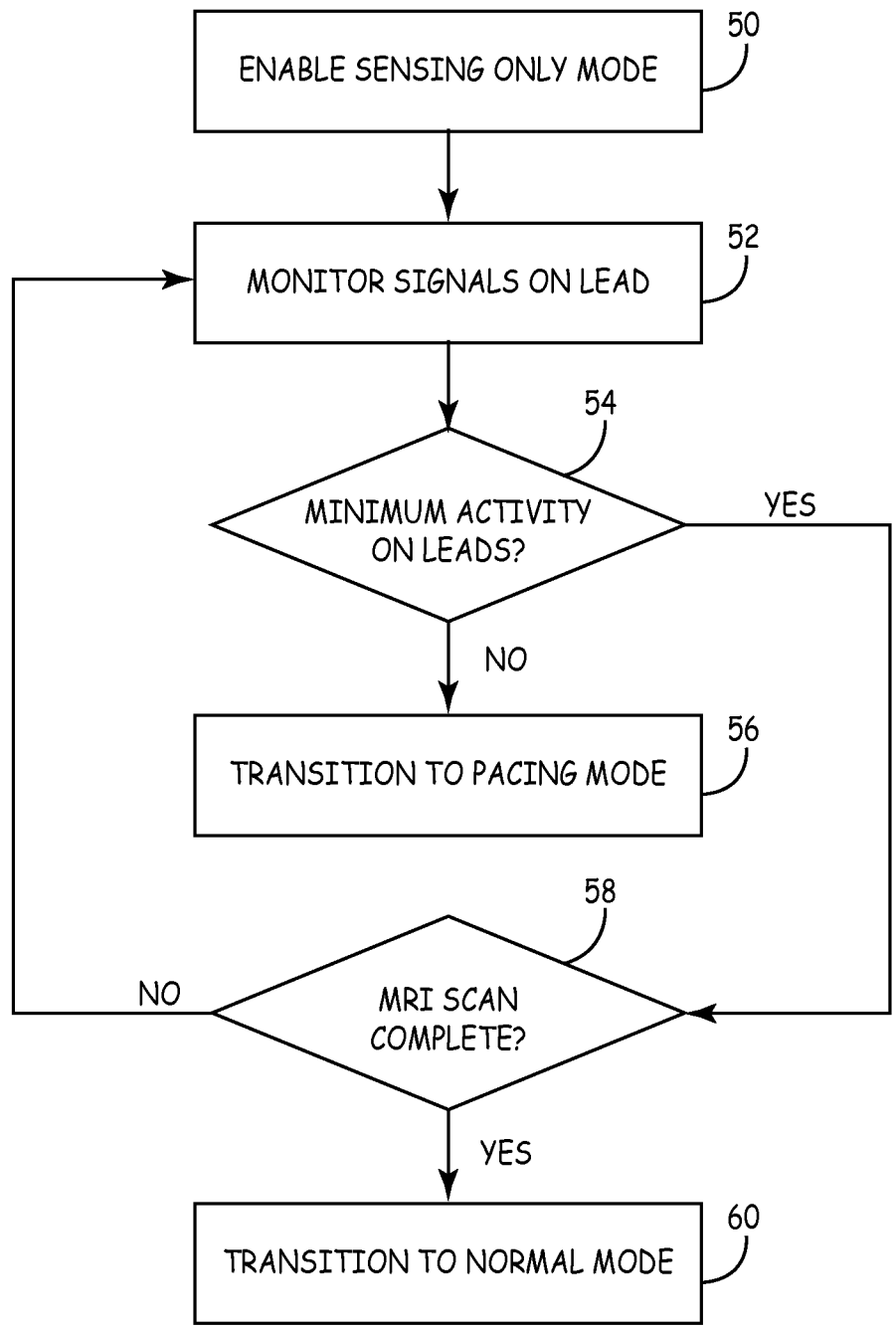
FIG. 4 is a flow diagram illustrating example operation of an implantable medical device in accordance with techniques of this disclosure.

FIG. 4 is a flow diagram illustrating example operation of an implantable medical device, e.g., IMD 14, operating in accordance with the techniques of this disclosure. Control module 40 of IMD 14 is configured to operate IMD 14 in a sensing only mode (50). Control module 40 may, for example, be configured to operate IMD 14 in a sensing only mode prior to or upon being exposed to external field 11 to reduce the effects of external field 11.

In the sensing only mode, control module 40 continues to monitor signals on one or both leads 15a,b (52). In examples in which there are more than two leads, control module 40 may monitor signals on all or a portion of the leads. Control module 40 determines whether there is a minimum amount of activity (e.g., sensed signals) on either one or both of leads 15a,b (54) and transitions from the sensing only mode to a pacing mode in response to not detecting the minimum amount of activity on one or both of leads 15a,b (56). In one example, control module 40 may transition to a pacing mode in response to not detecting a minimum number of events on one or both of leads 15a,b for a period of time, e.g., 2-3 seconds. In another example, control module 40 may transition from the sensing only mode to the pacing mode in response to detecting loss of more than one expected cardiac events, e.g., missing 2 out of 6 expected events. As described above, the reduction of sensed signals below the minimum level may correspond with the need for pacing support to prevent syncope or other adverse events. IMD 14 may therefore transition from the sensing only mode to the pacing mode to provide desired or needed therapy before, during or after the MRI or other procedure.

When control module 40 senses at least the minimum level of sensed signals on one or both leads 15a,b, control module 40 determines whether the MRI scan or other procedure is complete (58). Control module 40 may determine that the MRI scan is complete based on the output of external field detector 46 no longer indicating detection of external field 11, after expiration of a timer or a combination thereof. Alternatively, control module 40 may determine the MRI scan is completed in response to receiving a command from an external device 18.

When control module 40 determines the MRI scan is has not been completed, control unit 40 continues to monitor signals on one or both leads 15a,b (52). When control module 40 determines the MRI scan has been completed, control unit 40 transitions operation of IMD 14 to a normal operating mode (60). The normal operating mode may be the same or different from the pacing mode.

While the preceding description has been described primarily with reference to exposure to an environment 10 including an MRI device 16, the techniques of this disclosure may be used in environments with other devices that generate external fields that may affect operation of IMD 14. In fact, the techniques of this disclosure may be utilized in any context (medical or non-medical) in which IMD 14 is programmed into a sensing only mode, whether or not IMD 14 is exposed to an external field 11.

Additionally, the techniques described herein may be applicable to other therapy systems. For example, the techniques described herein may be applicable to systems including an IMD that delivers electrical stimulation therapy to other muscles, nerves or organs of patient 12. As another example, the techniques described herein may be applicable to systems including an implantable drug delivery or infusion device or an IMD including a drug delivery or infusion module. Other combinations of implantable devices will be obvious to one of skill in the art, and fall within the scope of this disclosure.

The techniques described in this disclosure, including those attributed to IMD 14, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, or flash memory, magnetic data storage media, optical data storage media, or the like. The instructions may be executed to support one or more aspects of the functionality described in this disclosure.

Various examples have been described. These and other examples are within the scope of the following claims.

The invention claimed is:
1. A method comprising:
transitioning operation of the implantable medical device to a first exposure operating mode in which the implantable medical device does not provide pacing prior to or upon the implantable medical device being exposed to an environment having one or more external fields known to possibly cause undesirable effects on the implantable medical device;

monitoring signals on at least one lead while operating in the first exposure operating mode; and upon failing to sense a minimum number of signals on the at least one lead while operating in the first exposure operating mode, transitioning operation of the implantable medical device from the first exposure operating mode to a second exposure operating mode in which the implantable medical device provides pacing that is not responsive to sensing.

2. The method of claim 1, wherein transitioning operation of the implantable medical device comprises transitioning operation of the implantable medical device from the first exposure operating mode to the second exposure operating mode upon failing to sense a signal on the at least one lead for a threshold period of time.

3. The method of claim 1, wherein transitioning operation of the implantable medical device comprises transitioning operation of the implantable medical device from the first exposure operating mode to the second exposure operating mode upon failing to sense a signal on the at least one lead for at least two seconds.

4. The method of claim 1, wherein transitioning operation of the implantable medical device from the first exposure operating mode to the second exposure operating mode upon failing to sense at least two expected cardiac events on the at least one lead within a window of time.

5. The method of claim 1, wherein transitioning operation of the implantable medical device from the first exposure operating mode to the second exposure operating mode upon failing to sense at least two expected cardiac events on the at least one lead within a particular number of expected events.

6. The method of claim 1, wherein operating the implantable medical device in the second exposure operating mode comprises operating the implantable medical device in one of an asynchronous pacing mode.

7. The method of claim 1, wherein sensing electrical signals on the lead while operating in the first exposure operating mode comprises sensing cardiac electrical signals and electrical signals induced by an external field on the lead while operating in the first exposure operating mode.

8. The method of claim 1, wherein the first exposure operating mode is a sensing only mode and the second exposure operating mode is an asynchronous pacing mode.

9. A system comprising:
at least one implantable medical lead that includes at least one electrode; and
an implantable medical device connected to the medical lead, the implantable medical device configured to transition to a first exposure operating mode in which the implantable medical device does not provide pacing prior to or upon the implantable medical device being exposed to an environment having one or more external fields known to possibly cause undesirable effects on the implantable medical device, monitor signals on the lead while operating in the first exposure operating mode, and upon failing to sense a minimum number of signals on the at least one lead while operating in the first exposure operating mode, transition to a second exposure operating mode in which the implantable medical device provides pacing that is not responsive to sensing.

10. The system of claim 9, wherein the implantable medical device transitions to the second exposure operating mode upon failing to sense a signal on the at least one lead for a threshold period of time.

11. The system of claim 9, wherein the implantable medical device transitions to the second exposure operating mode upon failing to sense a signal on the at least one lead for at least two seconds.

12. The system of claim 9, wherein the implantable medical device transitions to the second exposure operating mode upon failing to sense at least two expected cardiac events on the at least one lead within a window of time.

13. The system of claim 9, wherein the implantable medical device transitions to the second exposure operating mode upon failing to sense at least two expected cardiac events on the at least one lead within a particular number of expected events.

14. The system of claim 9, wherein the second exposure operating mode comprises one of an asynchronous pacing mode.

15. The system of claim 9, wherein the sensed signals comprises cardiac electrical signals and electrical signals induced on the medical lead by an external field.

16. The system of claim 9, wherein the first exposure operating mode is a sensing only mode and the second exposure operating mode is an asynchronous pacing mode.

17. A non-transitory computer-readable medium comprising instructions that, when executed, cause an implantable medical device to:
transition operation of the implantable medical device to a first exposure operating mode in which the implantable medical device does not provide pacing prior to or upon the implantable medical device being exposed to an environment having one or more external fields known to possibly cause undesirable effects on the implantable medical device;
monitor signals on at least one lead while operating in the first exposure operating mode; and
upon failing to sense a minimum number of signals on the at least one lead while operating in the first exposure operating mode, transition operation of the implantable medical device from the first exposure operating mode to a second exposure operating mode in which the implantable medical device provides pacing that is not responsive to sensing.

18. The non-transitory computer-readable medium of claim 17, wherein the instructions, when executed, cause the implantable medical device to transition operation of the implantable medical device from the first exposure operating mode to the second exposure operating mode upon failing to sense a signal on the at least one lead for a threshold period of time.

19. The non-transitory computer-readable medium of claim 17, wherein the instructions, when executed, cause the implantable medical device to transition operation of the implantable medical device from the first exposure operating mode to the second exposure operating mode upon failing to sense at least two expected cardiac events on the at least one lead within a particular number of expected events.

20. The non-transitory computer-readable medium of claim 17, wherein the first exposure operating mode is a sensing only mode and the second exposure operating mode is an asynchronous pacing mode.

* * * * *